United States Patent [19]

Trapasso et al.

[11] Patent Number: 5,554,785
[45] Date of Patent: Sep. 10, 1996

[54] ORGANOTIN CATALYZED TRANSESTERIFICATION PRODUCTS

[75] Inventors: Louise E. Trapasso, West Long Branch, N.J.; Stanley J. Padegimas, Memphis, Tenn.; Peter F. Epstein, Neptune City, N.J.; Paul L. K. Hung, Watchung, N.J.; Purnendu Mukhopadhyay, Sayreville, N.J.; Philip L. Meisel, Greenbrook, N.J.

[73] Assignee: CPS Chemical Company, Inc., Old Bridge, N.J.

[21] Appl. No.: 473,188

[22] Filed: Jun. 7, 1995

Related U.S. Application Data

[63] Continuation-in-part of Ser. No. 116,448, Sep. 19, 1993, Pat. No. 5,498,751.

[51] Int. Cl.$^6$ ................................................. C07C 69/34
[52] U.S. Cl. ................................................. 560/201
[58] Field of Search ........................... 560/190, 201, 560/198, 221

[56] References Cited

U.S. PATENT DOCUMENTS

| | | |
|---|---|---|
| 3,328,439 | 6/1967 | Hamilton . |
| 3,642,877 | 2/1972 | Madhusudan . |
| 3,663,569 | 5/1972 | Lew . |
| 3,686,768 | 8/1972 | Jobert et al. . |
| 3,714,234 | 1/1973 | White . |
| 4,112,235 | 9/1978 | Schmerling . |
| 4,229,362 | 10/1980 | Norman . |
| 4,281,175 | 7/1981 | Kametani et al. . |
| 4,301,297 | 11/1981 | Kametani et al. . |
| 4,473,702 | 9/1984 | Seguchi . |
| 4,547,585 | 10/1985 | Yamanaka et al. . |
| 4,667,044 | 5/1987 | Nees et al. . |
| 4,677,225 | 6/1987 | Nizuma et al. . |
| 4,745,213 | 5/1988 | Schlosser et al. . |
| 4,845,266 | 7/1989 | Marx et al. . |
| 4,904,814 | 2/1990 | Frei et al. . |
| 4,983,761 | 1/1991 | Brewer et al. . |
| 5,286,896 | 2/1994 | Korte et al. . |
| 5,338,882 | 8/1994 | Korte et al. . |

FOREIGN PATENT DOCUMENTS

| | | |
|---|---|---|
| 394571 | 5/1992 | Austria . |
| 85102522 | 7/1986 | China . |
| 262589 | 7/1989 | Czechoslovakia . |
| 4317428 | 6/1994 | Germany . |
| 54-41814 | 4/1979 | Japan . |
| 58170730 | 10/1983 | Japan . |
| 8637337 | 2/1986 | Japan . |
| 63115850 | 5/1988 | Japan . |
| 01265058 | 10/1989 | Japan . |
| 02067264 | 3/1990 | Japan . |
| 3041051 | 2/1991 | Japan . |
| 04095054 | 3/1992 | Japan . |

OTHER PUBLICATIONS

Yu et al., *Huaxue Xuebao*, 48(3), 287–94 (1990).
Otera et al., *Tetrahedron Lett.*, 27(21), 2383–6 (1986).
Otera et al., *J. Org. Chem.*, 54, 4013–(1989).
Otera et al., *J. Org. Chem.*, 56(18), 5307–11 (1991).
Aldrich, 33, 568–1, 1992.
Chemical Abstracts, CasOnline Printout; Matsuda An: 91:192843, rn=15625-89-59, 1976.

*Primary Examiner*—Samuel Barts
*Attorney, Agent, or Firm*—Lerner, David, Littenberg, Krumholz & Mentlik

[57] ABSTRACT

Esters of acrylic and methacrylic acid with alcohols and polyols having levels of purity greater than about 95% as measured by gas chromatography using an 11 meter RT×200 trifluoropropylmethyl polysiloxane column, a flame ionization detector, an injection temperature of 200° C., an initial column temperature of 90° C. for two minutes, followed by heating to 270° C. at a rate of 8° C. per minute and a detector temperature of 300° C.

16 Claims, No Drawings

5,554,785

ORGANOTIN CATALYZED TRANSESTERIFICATION PRODUCTS

This application is a Continuation-In-Part of U.S. patent application Ser. No. 08/116,448, filed Sep. 3, 1993, now U.S. Pat. No. 5,498,751, the disclosure of which is incorporated herein by reference.

BACKGROUND OF THE INVENTION

The present invention relates to methods for producing higher esters of carboxylic acids by an organotin catalyzed transesterification reaction between lower alkyl esters of the carboxylic acid and alcohols and polyols. In particular, the present invention relates to novel methods for forming heretofore unattainable 1,2- and 1,3-polyol esters by organotin catalyzed transesterification. In addition, the present invention relates to methods for synthesizing such polyol esters, as well as other polyol and alcohol esters, by organotin catalyzed transesterification, and recovering the resulting esters substantially free of the organotin catalyst.

Esters of unsaturated carboxylic acids and of aromatic polycarboxylic acids are of increasing commercial importance as polymerizable monomers. Materials of this nature are used to form both homopolymers and copolymers; which have commercial uses in many applications. Such applications include coatings for paper products, waste water treatment systems, optical lens coatings, floor polishes, anaerobic adhesives, pour point depressants, paper coatings, UV and EB coatings and adhesives, textile finishes, pressure sensitive adhesives, viscosity index improvers, potting compounds and sealants, photopolymers for electronics and printing plates, rubber and plastics modifiers, UV curable inks and overprint varnishes, dental and medical resins, reactive diluents for radiation curable oligomers, crosslinkers for rubber vulcanization, moisture barrier films, ion exchange resins, PVC plastisols, encapsulation and impregnation of small diameter spheres, leather finishes, binder resins for sand castings, UV curable resins for imaging systems, silane intermediates, and the like; such applications being well known to those skilled in the art.

One group of monomers of particular interest are the polyfunctional monomers; that is to say, esters of unsaturated carboxylic acids with polyfunctional alcohols. As is also well known to those skilled in the art, materials of this nature can be used as cross-linking agents to form rigid coatings which are insoluble in normally-used solvents. Of particular interest are the esters of acrylic acid (2-propenoic acid) and methacrylic acid (2-methyl-2-propenoic acid). These esters, both monofunctional and polyfunctional, have long been used as components of homopolymers and/or copolymers for the applications described above.

Another group of monomers of particular interest are the unsaturated esters of aromatic polycarboxylic acids. The polymerization products of such monomers possess excellent dielectric properties, dimensional stability, heat resistance, weatherproof-ness, solvent resistance and mechanical properties. Preferred polymer products also possess optimum optical properties, including transparency, refractive index and surface hardness. Such polymers are desirable for use as optical materials.

In the past, as in current industrial practice, the above monomers have been made by direct esterification, i.e., the acid catalyzed reaction of an unsaturated carboxylic acid with a mono- or polyhydric alcohol. The major exception to this procedure is the preparation of unsaturated esters containing a basic functional group, such as an amine group. In these cases, the products have traditionally been made by a transesterification procedure, using catalysts such as sodium methylate, lead oxide, tetraisopropyl titanate, and the like. (See, e.g., U.S. Pat. No. 3,642,877.) In the commercial preparation of compounds of this type, the final reaction mixture is subjected to fractional distillation under reduced pressure, in order to obtain the desired monomer in a state of high purity, free of the metallic catalyst and/or excess polymerization inhibitor, which must be present during the preparation of these compounds.

By contrast, the products of the acid-catalyzed direct esterification are purified by base-washing procedures, which will remove acid catalyst and excess unreacted carboxylic acid as well as excess polymerization inhibitors. Although, in principle, it would be possible also to purify such reaction products by fractional distillation under reduced pressure, in industrial practice this procedure is only used with materials of relatively high volatility. This is because many of these products, particularly the esters of long-chain aliphatic alcohols as well as the esters of polyhydric alcohols, have relatively high boiling points, even when high vacuum is employed. In industrial practice it is very difficult to attain pressures less than about 1 mm Hg (more usually the vacuum used varies from about 10 to 20 mm Hg); and even under these conditions, the boiling points of these esters are so high as to make them very difficult to distill. As is well known in the art, monomers of this nature will tend to polymerize at temperatures in excess of about 115° C.–120° C., even when inhibited with various polymerization inhibitors. Consequently, in industrial practice, it is preferred to isolate the reaction products as "bottoms" products, which are not distilled.

The acid-catalyzed direct esterification described above suffers from various disadvantages, particularly the occurrence of several side reactions. In particular, such processes may cause the formation of color bodies which may be difficult, if not impossible, to remove from the finished product. Such color bodies may render the product unsuitable for many industrial applications, in particular in areas such as paper treatment chemicals, industrial coatings and the like. Also, the acid-catalyzed side reactions will lead to the production of by-products. Such by-products, although not necessarily deleterious in themselves, act as unreactive diluents for the final product and thus reduce its efficacy. Other disadvantages include the need to use an excess of the carboxylic acid to complete the reaction. This excess carboxylic acid cannot generally be recovered and recycled; and therefore represents an extra raw material cost as well as an increased waste disposal cost.

It is, of course, possible to prepare many of these products by transesterification, but many of the same disadvantages will remain. In particular, many potential transesterification catalysts such as aluminum isopropoxide, sodium methoxide, tetraisopropyl titanate and lead oxide, also catalyze the same side reactions described above. A further disadvantage is that many of these catalysts are difficult, if not impossible, to remove from the finished product, especially on an industrial scale.

The multifunctional acrylates and methacrylates that are used as reactive diluents in coating formulations are described and referred to in commercial literature as if they are well defined discrete chemical substances. In actuality, materials like trimethylpropane triacrylate (TMPTA) and tripropylene glycol diacrylate (TPGDA) have been poorly characterized in commercial and trade literature. R. H. Hall, et al were the first to publish a report on the chemistry and the chemical analysis of these materials in a paper entitled, "Just How Pure Are Your Monomers? A Chemical Analysis Of Some Common Reactive Diluents". The paper was presented at the Radcure Europe '85 Conference, May 6–8, 1985; Basel, Switzerland. Using modern analytical techniques, the authors demonstrated that these products, as prepared by esterification of the respective diol or polyol with acrylic acid (AA), contain not only simple acrylate ester components but also products formed by addition of acrylic acid to the esters and by addition of hydroxyl-functional acrylates to the unsaturated double bonds of other acrylates. These addition products are higher boiling components generally referred to as Michael adducts. They concluded, for example, that at that time the quantity of TMPTA present in commercially available samples was no more than about 50%.

Commercially available TMPTA made by direct esterification has a color of about 50–100 APHA and a viscosity greater than 100 cps. A higher purity product would not only lower color and viscosity, but double bond functionality would increase as well. The significance of this to the radiation cure end-user is that cure rates are enhanced and greater latitude in formulating becomes possible. That is, higher double bond functionality translates into a faster cure rate and a higher radiation quantum yield enabling a higher rate of speed through the radiation chamber for higher productivity. A lower viscosity allows a higher pigment and coating vehicle loading that results in improved coating properties. Lower color would insure true pigment color values and enhanced clarity and luster to the cured coating composition.

The analytical methods generally used to quantify the purity of multifunctional acrylates and methacrylates do not accurately reflect their true purities. The deficiencies of the analytical methods used can be demonstrated by the manner in which specifications and analytical test methods are selected by suppliers.

Using TMPTA as an illustration, the leading supplier of multifunctional acrylates and methacrylates (UCB Radcure Inc.) chooses not to report a purity level. In place of a purity specification, UCB Radcure uses an Ester Rank specification, which is a value derived from a Saponification Equivalent test performed on a weighed sample. An Ester Rank of 2.7 indicates that 2.7 out of 3.0 of the available hydroxyl groups have been esterified. This is a misleading representation of purity, since all esters present, even those without double bonds, have a saponification value and are counted as if they were TMPTA. Likewise, Henkel Corporation uses an Ester Rank specification in lieu of reporting purity for the TMPTA it produces.

The other major supplier (Sartomer Chemical Company) uses a gas chromatography (GC) technique (20% SE 30 methyl silicone column on 80/100 mesh Chromosorb WHP, 6ft×⅛ inch, stainless steel) with a high injection port temperature (250° C.), a rapid temperature ramp (i.e. initial temperature 80° C., ramp at 20° C./min to 300° C.) and a thermal conductivity detector at 320° C. The major peak demonstrated by the GC analysis is TMPTA and its purity (area %) is represented as at least 88% by Sartomer's specification. This, however, is an artifact of the Chromatographic technique. As noted above, prior art esterification technology results in the formation of higher boiling Michael adduct byproducts in addition to the acrylate ester. Thus, substantial quantities of Michael adducts are present which have been formed by the addition reaction of TMP triacrylate (TMPTA), TMP diacrylate (TMPDA) or TMP monoacrylate (TMPMA) with acrylic acid or each other.

Significantly, the chromatographic techniques of Sartomer and Aldrich (i.e. using a DB-1 (J&W) methyl silicone column—see below for details of Aldrich's analytical technique) have a inherent bias that underestimates the quantities of Michael adduct byproduct present, resulting in artificially high purity values for TMPTA.

Metal-containing catalysts, such as tetraisopropyl titanate, aluminum isopropoxide or dibutyltin oxide, can be used as catalysts for transesterification reactions of monofunctional (monohydric) alcohols, as well as of polyhydric alcohols in which the hydroxyl groups are not in close proximity. However, in the case of vicinal polyols, such as ethylene glycol, 1,2-propanediol and glycerol; or in the case of polyols where the hydroxyl groups occupy 1,3-positions, such as 1,3-propanediol, trimethylolpropane, or 1,3-butanediol; metallic catalysts, such as the ones mentioned above, form, respectively, five or six-membered metal-containing cyclic compounds. These cyclic compounds are relatively unreactive and will participate only slightly, if at all, in the catalytic reaction steps needed to bring the transesterification reaction about in a reasonable length of time. It is, therefore, not feasible to use these materials as catalysts for the preparation of esters derived from the polyhydric alcohols described above.

Another metal-containing catalyst system made from dialkyltin dichlorides has recently been reported. Otera et al., *J. Org. Chem.*, 54, 4013–14 (1989) discloses that dialkyltin oxychloride dimers form a stable, rigid, ladder structure (with four tin atoms), which functions as a template that exercises steric control during transesterification. These materials have been described as "reverse micelles" whose structure has to remain intact in order to be catalytic. Hydrocarbon solvents are preferred, because polar solvents dissociate the complex, leading to poor catalytic activity. However, predominantly non-polar reaction solvents are undesirable for the transesterification of commercially desirable carboxylic acid monomers. In addition, this reference contains no disclosure regarding how to isolate the pure product ester, a step which is essential to commercial manufacture. Furthermore, these compounds are reported to hydrolyze and form tetraorgano distannoxanes.

Otera et al., *J. Org. Chem.*, 56(18), 5307–11 (1991) disclose these compounds to be effective catalysts in the transesterification of monohydric alcohols. This is confirmed by Otera et al., *Tetrahedron Lett.*, 27(21), 2383–6 (1986), which also discloses the transesterification of diols other than 1,2- and 1,3-diols.

U.S. Pat. No. 4,473,702 discloses the synthesis of a diallyl ester of an aromatic dicarboxylic acid by transesterification of a dialkyl ester of an aromatic dicarboxylic acid with allyl alcohol. The reaction is catalyzed by a dialkyltin dichloride, dialkyltin oxide or mixtures thereof in combination with a second catalyst such as metallic magnesium, zinc, tin, lead, aluminum, nickel or zirconium, or oxides thereof. The disclosure of this patent is limited to reactions employing monohydric alcohols and the resulting ester is separated by conventional distillation and recrystallization methods, with no indication that the ester is obtained in a pure form free of the metal catalyst.

None of the foregoing publications discloses a transesterification catalyst or method that will allow for transesterification of 1,2- and 1,3-polyols, or the isolation of pure product ester. There remains a need for a catalyst system effective in the transesterification of 1,2- and 1,3-polyols. A system that would permit the isolation of the pure ester product free of the metal catalyst would be even more desirable.

SUMMARY OF THE INVENTION

It has now been found that organotin catalysts can be used in an unexpectedly different manner than described in the above-cited references to provide heretofore unattainable transesterification products in high yield and of excellent purity. The process of the present invention provides a simplified method of catalyst removal and also eliminates the need for purification by distillation. The products prepared in accordance with the methods of the present invention are substantially colorless and free of by-products and metallic catalysts.

In accordance with the present invention, there are provided esters of acrylic and methacrylic acid with alcohols and polyols, which esters are selected from trimethylolpropane triacrylate, tripropylene glycol diacrylate, tetraethylene glycol diacrylate, 1,6-hexanediol diacrylate, 1,3-butylene glycol diacrylate, 2-phenoxyethyl acrylate, trimethylolpropane trimethacrylate, polyethylene glycol dimethacrylate, tetraethylene glycol dimethacrylate and 1,3-butylene glycol dimethacrylate. The esters have levels of purity greater than about 95% as measured by gas chromatography using an 11 meter RTx200 trifluoropropylmethyl polysiloxane column, a flame ionization detector, an injection temperature of 200° C., an initial column temperature of 90° C. for two minutes followed by heating to 270° C. at a rate of 8° C. per minute and a detector temperature of 300° C. Preferred esters have levels of purity greater than about 95%, and more preferred esters have purities greater than about 97%, up to about 99% and greater, as measured by the aforementioned procedure.

The acrylate and methacrylate esters of the present invention are recovered as liquids having the above-disclosed levels of purity. The esters are much lower in both color and viscosity than comparable commercially available direct esterification products. Color less than 20 APHA and Brookfield viscosities less than 46 cps are typical for acrylate and methacrylate esters made using the organotin catalyzed transesterification process of the present invention. Other features of the present invention will be pointed out in the following description and claims, which disclose, by the way of example, the principles of the invention and the best modes which have been presently contemplated for carrying them out.

DETAILED DESCRIPTION OF THE PREFERRED EMBODIMENT

The esters of the present invention can be prepared by the following transesterification reaction:

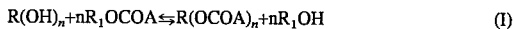

$$R(OH)_n + nR_1OCOA \rightleftharpoons R(OCOA)_n + nR_1OH \quad (I)$$

In this equation, $R(OH)_n$ represents the alcohol or polyol whose ester is to be prepared, $R_1OH$ is the monohydric alcohol whose ester is used in the transesterification reaction; and A represents the acid from which the esters are derived. The variable n is an integer whose value can be one or greater, preferably from one to four.

The transesterification process of the present invention is operative for essentially any mono- or polycarboxylic acid ester derivative. In the above-depicted reaction scheme, A can represent an aromatic, aliphatic or cycloaliphatic mono- or polycarboxylic acid residue. The aromatic carboxylic acid residues may be derived from single ring, multiple ring and fused ring system compounds. The carboxylic acid groups may be directly substituted on an aromatic ring, or part of an alkyl group that is substituted on the ring.

In addition, the aromatic ring may be further substituted with one or more groups selected from halogen, amino, cyano, nitro, and the like, as well as alkyl, alkoxy and alkylthio groups containing from 1 to 20 carbon atoms, and the like. The alkyl groups may be saturated or unsaturated, substituted or unsubstituted and branched or unbranched. The alkyl groups, when substituted, may contain one or more of the functional groups listed above as being suitable for aromatic ring substitution. The aromatic carboxylic acid residues represented by A preferably contain between about 7 and about 20, and more preferably contain between about 8 and about 12 carbon atoms.

The aliphatic and cycloaliphatic carboxylic acid residues may be derived from saturated, monounsaturated and polyunsaturated carboxylic acids. These acids may be straight-chained or branched and may be substituted with one or more of the groups listed above as being suitable for aromatic ring substitution. The aliphatic and cycloaliphatic carboxylic acid residues represented by A preferably contain between about 2 and about 40 carbon atoms, and more preferably contain between about 3 and about 26 carbon atoms.

While the transesterification method of the present invention is functional with respect to essentially any carboxylic acid ester starting material, esters of aromatic and unsaturated aliphatic and cycloaliphatic carboxylic acids are preferred because of the utility of their transesterification reaction as polymerization monomers. The unsaturated bonds of the aliphatic and cycloaliphatic carboxylic acid esters serve as polymerization sites for the monomers. The aromatic carboxylic acid esters, on the other hand, are preferably transesterified with an unsaturated alcohol, the double bonds of which serve as polymerization sites for the monomers. While the method of the present invention can be used to synthesize higher esters of saturated aliphatic and cycloaliphatic carboxylic acids and saturated esters of aromatic carboxylic acids, these materials, unlike the preferred compounds of the present invention, can be produced by the more vigorous reaction conditions of direct esterification, and it is not essential to prepare these materials by the relatively milder conditions of transesterification.

$R_1$ in the above-depicted reaction scheme represents the alcohol portion of the carboxylic acid ester starting material. The transesterification process of the present invention results in the formation of a monohydric alcohol containing this group. While $R_1$ can represent essentially any lower alkyl group for the transesterification process of the present invention to proceed, for all practical purposes, $R_1$ is methyl or ethyl. Methyl or ethyl ester starting materials are desirable for two reasons. First, such esters function to optimize the reaction temperature and the homogeneity of the reaction mixture. Second, as is well known to those skilled in the art, the transesterification reaction of the present invention is reversible. Therefore, in order to drive the reaction to completion, it is necessary to remove one of the reaction products from the system.

Although theoretically either the new ester $R(OCOA)_n$ or the new alcohol $R_1OH$ could be removed, the transesterification process of the present invention converts the ester starting material to methanol or ethanol, respectively. These lower boiling alcohols are much simpler to remove from the reaction product mixture by direct distillation or through the formation and distillation of lower boiling azeotropes, than are higher alcohols.

Particularly preferred mono- and polycarboxylic acid ester starting materials include methyl and ethyl acrylate, methyl and ethyl methacrylate, methyl and ethyl benzoate, methyl and ethyl phthalate, methyl and ethyl trimellitate, methyl and ethyl terephthalate, methyl and ethyl isophthalate, methyl and ethyl naphthalene di- and tricarboxylates, methyl and ethyl benzene tricarboxylates, and the like. The transesterification process of the present invention will produce higher esters of these carboxylic acids.

R of the above-depicted reaction scheme represents the alcohol portion of the ester to be formed in the transesterification reaction of the present invention, with $R(OH)_n$ representing the monohydric or polyhydric alcohol starting material whose ester is to be prepared. For purposes of the present invention, R will be defined as the residue of the alcohol or polyol starting material whose ester is to be prepared by the disclosed transesterification process.

In the processes of the present invention, R represents the residue of an aralkyl, aliphatic or cycloaliphatic alcohol or polyol. The hydroxyl groups of the aralkyl alcohols or polyols are alkyl-substituted. The aralkyl alcohols and polyols from which the residue R may be derived may contain a single or multiple aromatic ring or a fused ring system. Any aromatic ring may be substituted or unsubstituted. Substituted aromatic rings may contain the ring substituents described above with respect to the aromatic rings of the aromatic carboxylic acid ester starting material. Aralkyl alcohol and polyol residues in accordance with the present invention preferably contain between about 7 and about 20 carbon atoms, and more preferably contain between about 8 and about 12 carbon atoms.

The aliphatic or cycloaliphatic alcohols and polyols from which the residue R is derived may be saturated, monounsaturated or polyunsaturated. The alcohol and polyol residues may be straight-chained or branched, and substituted or unsubstituted. The substituted residues may include one or more of the groups described above as being suitable for ring substitution of the aromatic carboxylic acid starting materials of the present invention. The alcohol and polyol residues represented by R preferably contain between about 2 and about 40 carbon atoms, and even more preferably contain between about 3 and about 26 carbon atoms.

Particularly preferred alcohols and polyols for use in the transesterification process of the present invention include n- or iso- 8 to 22 carbon atom alkanols, furfuryl alcohol, tetrahydrofurfuryl alcohol, benzyl alcohol, 2-phenoxyethanol, cyclohexanol, allyl alcohol, methallyl alcohol, crotyl alcohol, ethylene glycol, triethylene glycol, tripropylene glycol, tetraethylene glycol, 1,6-hexanediol, 1,3-butylene glycol (1,3-butanediol), polyethylene glycol, 1,4-butanediol, trimethylolpropane, pentaerythritol, dipentaerythritol, 2,2-dimethyl-1,3-propanediol, glycerine, and the like. When reacted with methyl or ethyl acrylate or methacrylate, the transesterification process of the present invention produces higher esters of acrylic or methacrylic acid.

The transesterification process of the present invention provides alcohol and polyol esters of acrylic or methacrylic acid having levels of purity greater than about 95% measured by gas chromatography using an 11 meter RTx200 trifluoropropylmethyl polysiloxane column, a flame ionization detector, an injection temperature of 200° C., an initial column temperature of 90° C. for two minutes followed by heating to 270° C. at a rate of 8° C. per minute and a detector temperature of 300° C. As will be understood by those of ordinary skill in the art, levels of purity greater than about 97%, up to about 99% and greater, as measured by the aforementioned procedure, may be achieved using purer reactants, longer reaction times, increased reaction temperatures, higher concentrations of rate limiting reactants and by utilizing techniques for stripping lower molecular weight contaminants.

Thus, the present invention provides trimethylolpropane triacrylate (TMPTA) having a level of purity greater than heretofore available, i.e., greater than about 82% as measured by the above GC technique. Purity levels greater than about 88% are preferred, and levels greater than about 92% are even more preferred.

Tripropylene glycol diacrylate (TPGDA) prepared according to the present invention will have a level of purity of at least about 92% as measured by the above-described GC technique.

Tetraethylene glycol diacrylate (T4EGDA) prepared according to the present invention will have a level of purity of at least about 92% as measured by the same GC technique.

1,6-hexanediol diacrylate (HDDA) prepared according to the present invention will have a level of purity of at least about 95% as measured by the GC technique described herein.

1,3-butylene glycol diacrylate (1,3-BGDA) prepared according to the present invention will have a level of purity greater than about 88% as measured by the above GC procedure. Purity levels greater than about 92% are preferred.

2-phenoxyethyl acrylate (PEA) prepared according to the present invention will have a level of purity greater than about 92% as measured by the above GC procedure.

Trimethylolpropane trimethacrylate (TMPTMA) prepared according to the present invention will have a level of purity greater than about 92% as measured by the above GC procedure.

Polyethylene glycol dimethacrylate (PEG200DMA) and tetraethylene glycol dimethacrylate (T4EGDMA) prepared according to the present invention will all have levels of purity of at least about 92% as measured by the above GC procedure.

1,3-butylene glycol dimethacrylate (1,3-BGDMA) prepared according to the present invention will have a level of purity of at least about 92% as measured by the above GC procedure.

The transesterification process of the present invention is operative for the combination of essentially any aralkyl, aliphatic or cycloaliphatic polyol starting materials with essentially any aromatic, aliphatic or cycloaliphatic monocarboxylic acid, or with any aralkyl, aliphatic or cycloaliphatic alcohol with essentially any aromatic, aliphatic or cycloaliphatic mono- or polycarboxylic acid. The combination of polyols with polycarboxylic acids is undesirable because the reactants crosslink to form non-useful reaction products.

Again, the process of the present invention is particularly well suited for unsaturated starting materials, because unsaturated alcohols, polyols and carboxylic acids are sensitive to the more vigorous direct esterification conditions. Commercially useful monomers are typically obtained by reacting an aralkyl or saturated aliphatic or cycloaliphatic alcohol with an unsaturated aliphatic or cycloaliphatic mono- or polycarboxylic acid ester, or by reacting an unsaturated alcohol with an aromatic or saturated aliphatic or cycloaliphatic mono- or polycarboxylic acid ester. Commercially useful monomers are also obtained by reacting an aralkyl or saturated aliphatic or cycloaliphatic polyol with an unsaturated aliphatic or cycloaliphatic monocarboxylic acid ester.

Unexpectedly unique results, however, are obtained for 1,2- and 1,3-polyols with the dialkyltin catalyst system of the present invention. The catalyst system provides for the high yield and high purity transesterification of such polyols without the formation of five- and six-membered metal-containing cyclic compounds that plague prior art transesterification methods. The unexpected results are obtained for the transesterification of essentially any monocarboxylic acid ester with the 1,2- and 1,3-polyols. It is also envisioned that a prepolymer could be prepared by reacting a dicarboxylic acid ester with a diol by using the art of this invention, but in this case, the molar ratio of diol to ester must be other than one to avoid forming a high viscosity product.

Unexpectedly unique results are also obtained for the transesterification of essentially any alcohol with essentially any mono- or polycarboxylic acid ester, or for the transesterification of essentially any polyol with essentially any monocarboxylic acid ester, using the dimethyltin catalyst systems of the present invention. When a dimethyltin catalyst system is employed, the transesterification product obtained after simple alkaline washing is essentially free of the organotin catalyst.

The above-depicted reaction scheme is carried out by first charging a reactor with the alcohol or polyol, followed by the methyl or ethyl ester of the mono- or polycarboxylic acid. The molar ratio of the methyl or ethyl ester of the carboxylic acid to the alcohol or polyol can be varied over a wide range, but is always greater than 1.0. Preferably, the ratio lies between about 1.2:1 and 5:1 of the methyl or ethyl carboxylic acid ester per mole of hydroxyl functionality.

A reaction temperature is selected at which the alcohol or polyol and the methyl or ethyl carboxylic acid ester are liquid. This will vary considerably because of the wide variety of carboxylic acid esters, alcohols and polyols that can be utilized with the inventive process. However, the selection of a reaction temperature at which the reactants are liquid is a matter that can be readily determined by one of ordinary skill in the art without undue experimentation. Typically, the reaction temperature will range between about 60° C. and about 140° C., and usually between about 80° C. and about 120° C.

The reaction is carried out in the presence of a dialkyltin catalyst system. Typically, the catalyst system is present at a level between about 0.01 and about 2.00 percent by weight, and more preferably at a level between about 0.05 and about 1.00 percent by weight. To obtain the transesterification of 1,2- and 1,3-polyols, a dialkyltin catalyst system consisting of dialkyltin dichloride and dialkyltin oxide is used. Maintenance of an equal stoichiometric ratio of dialkyltin dichloride to dialkyltin oxide is preferred in order to enhance the reaction rate.

Dialkyltin dichlorides and dialkyltin oxides having alkyl groups containing between 1 and 12 carbon atoms are suitable for use with the present invention. For the transesterification of 1,2- and 1,3-polyols, mixtures of dibutyltin oxide or dimethyltin oxide with either dibutyltin dichloride or dimethyltin dichloride are particularly effective. A mixture of dimethyltin oxide with dimethyltin dichloride is particularly preferred, because this catalyst system is readily removed from the reaction mixture to obtain a reaction product essentially free of the organotin catalyst blend.

Another feature of the method of the present invention for the transesterification of 1,2- and 1,3-polyols is that the dialkyltin oxide-dialkyltin dichloride catalyst blend can be prepared in situ. The catalyst blend is formed in situ by including dialkyltin dichloride in the reaction mixture, which partially converts to the dialkyltin oxide under reaction conditions, although the transesterification reaction rate is initially slower at first until an effective quantity of the dialkyltin dichloride has converted to the dialkyltin oxide.

The in situ formation of the dialkyl dichloride-dialkyltin oxide blend can be promoted by the addition of an HCl-acceptor or alkali base to the reaction mixture, such as an alkali metal hydroxide or alkoxide, an alkaline earth metal hydroxide or oxide, an alkali or alkaline earth metal carbonate or bicarbonate, tribasic alkali phosphates, organic bases such as tertiary amines, and the like. Preferred alkali metals include lithium, sodium and potassium. Preferred alkoxides include methoxides such as sodium methylate, sodium ethoxides and sodium alkoxides of the alcohol to be transesterified. The preferred alkaline earth metal is magnesium and calcium, and the preferred tertiary amine is triethylamine. The molar ratio of the HCl-acceptor to dialkyltin dichloride can be varied over a wide range, but in general, the best results are obtained for polyhydric alcohols with a molar excess of dialkyltin dichloride.

While the nature of the alkyl groups attached to the tin atom in the dialkyltin dichlorides and oxides suitable for use in the transesterification process of the present invention can vary widely, dimethyltin dichloride and dimethyltin oxide are preferred, based upon their solubility in excess alkali and, consequently, their ready removability from the reaction mixture upon completion of the transesterification. This solubility in alkali permits the design of the commercial process in which a transesterification ester reaction product is obtained essentially free of the organotin catalysts, a property that has heretofore been unexploited. The higher dialkyltin oxides, such as dibutyltin oxide, which are either included as part of a catalyst blend, or generated in situ from dialkyltin dichlorides such as dibutyltin dichloride, form insoluble precipitates when treated with excess alkali. These precipitates are difficult to remove from the ester reaction product upon completion of the transesterification reaction.

More particularly, dimethyltin dichloride, dimethyltin oxide, and any combinations thereof, are completely soluble in aqueous alkali solutions, provided that the pH of these solutions is greater than about 13.2. Accordingly, organotin compound contamination of the transesterification reaction product can be prevented by washing the reaction mixtures at pH's of about 13.2 and greater. This is emphatically not the case with the corresponding dibutyltin compounds. For this reason, dimethyltin dichloride and dimethyltin oxide are the most preferred organotin catalysts for use in the processes of the present invention. The desired result can be obtained with reaction mixture pH's greater than about 13.2.

Dibutyltin compounds were listed above as among the preferred dialkyltin catalysts for the transesterification of 1,2- and 1,3-polyols. Unlike the dimethyltin catalysts, these compounds are not soluble in aqueous alkali solutions, and therefore cannot be removed from the carboxylic acid ester transesterification product by contact therewith. Dibutyltin compounds can, however, be removed from the reaction mixture at the end of the transesterification by extraction with an aqueous solution of a mineral acid or strong organic acid. Mineral acids suitable for extraction of dibutyltin compounds include hydrochloric and sulfuric acids. A suitable strong organic acid is methanesulfonic acid.

While the dimethyltin compounds are particularly preferred in the transesterification of 1,2- and 1,3-polyols so that the carboxylic acid ester reaction product is readily obtained essentially free of the residual catalyst, this concept can be extended to the transesterification of other polyols, as well as to the transesterification of alcohols. Carboxylic acid esters of these alcohols and polyols can also be readily obtained essentially free of the dimethyltin compounds by washing reaction mixtures with aqueous caustic such that the aqueous phase has pH's greater than about 13.2.

Because such mixtures of dialkyltin dichlorides and dialkyltin oxides do not form five- or six-membered tings in the presence of 1,2- and 1,3-polyols, mixtures of dimethyltin dichloride and dimethyltin oxide are suitable transesterification catalysts for these polyols. Consequently, blends of dimethyltin dichloride and dimethyltin oxide, when employed, may be directly added to the reaction mixture, or formed in situ by adding dimethyltin dichloride to the reaction mixture and partially converting it to dimethyltin oxide. This procedure can be used, even with substrates in which the ring formation described above does not occur. Again, the conversion can be accelerated by adding to the reaction mixture an HCl-acceptor compound or alkali base. For the transesterification of polyols, a molar excess of dimethyltin dichloride over the HCl-acceptor should be employed. For the transesterification of mono-alcohols, a stoichiometric deficiency of dimethyltin dichloride should be employed.

The foregoing is not meant to imply that dialkyltin dichlorides, dialkyltin oxides and mixtures thereof cannot be generally used to transesterify monohydric alcohols or polyols other than 1,2- and 1,3-polyols. However, the dimethyltin catalyst system of the present invention readily provides a carboxylic acid ester transesterification reaction product essentially free of the organotin catalysts.

Therefore, esters of carboxylic acids prepared in accordance with the dimethyltin catalyzed transesterification processes of the present invention will contain less than about 100 ppm of organotin compounds. The reaction product will preferably contain less than about 10 ppm organotin compounds, and ideally contain less than about 2 ppm of organotin compounds.

For transesterification reactions utilizing unsaturated carboxylic acid ester starting materials, or unsaturated monohydric or polyhydric alcohol starting materials, it is critical that polymerization of the unsaturated bonds be inhibited with one or more polymerization inhibitors. Such inhibitors are well know to those skilled in the art and include, but are not limited to, hydroquinone and its monomethyl ether, catechol, pyrocatechol, resorcinol, pyrogallol, propyl gallate, and the like.

A common feature of the above-described polymerization inhibitors is that they require the presence of oxygen to function effectively. It is, therefore, necessary to supply a stream of an oxygen-containing gas (either air or an air-nitrogen mixture) to the reaction vessel throughout the course of the transesterification reaction when such polymerization inhibitors are employed. The amount of oxygen to be used depends upon the exact product being made as well as on the size of the reactor, and can be readily determined by one of ordinary skill in the art without undue experimentation.

Another feature common to the above-listed polymerization inhibitors is that they all contain one or more phenolic hydroxyl groups. The presence of these phenolic groups enables the inhibitors to form water-soluble sodium salts when contacted with sodium hydroxide solutions. This permits the easy removal of excess phenolic inhibitors from the reaction mixture at the end of the reaction, if desired. Also, as is well understood by those of ordinary skill in the art, if desired, lower levels of inhibitors and/or different inhibitors can be added at this point. In addition, the alkali solubility of the polymerization inhibitors permits the removal from the carboxylic acid ester transesterification reaction product both the polymerization inhibitor and the residual dimethyltin transesterification catalyst by the same washing procedure.

As noted above, in order to drive the transesterification reaction of the present invention to completion, it is necessary to remove one of the reaction products from the system. Because of its lower boiling point, the ethanol or methanol generated by the transesterification is the more practical reaction product to remove. Depending upon the other reactants and reaction products, it may be possible to directly distill off the methanol or ethanol. However, in many cases, the methanol or ethanol generated will form azeotropes with the corresponding methyl or ethyl carboxylic acid ester starting material. This can be advantageous because the azeotropes generally have lower boiling points than the alcohols themselves, permitting an even simpler removal of the methanol or ethanol by distillation of the azeotrope as the alcohol is generated by the transesterification reaction. Alternatively, the methanol or ethanol may be removed by the addition of an auxiliary solvent to the reaction mixture, such as an aliphatic hydrocarbon solvent with which the alcohol forms an even lower boiling azeotrope. This permits removal of the alcohol as it is formed by the transesterification reaction without removing the methyl or ethyl carboxylic acid ester starting material which is needed for the reaction to proceed.

Thus, the reaction mixtures of the transesterification processes of the present invention may optionally include up to about 30 percent by weight, and preferably between about 5 and about 15 percent by weight of a hydrocarbon solvent among the starting materials to form a lower boiling methanol or ethanol azeotrope to assist in removing methanol or ethanol and drive the equilibrium of the transesterification reaction forward. Suitable hydrocarbon solvents include aliphatic and cycloaliphatic hydrocarbons having from about four to about eight carbon atoms. Six or seven carbon atom hydrocarbon isomer mixtures are preferred. The hydrocarbon solvent can be regenerated from the azeotrope by washing with water to extract the methanol or ethanol. The hydrocarbon solvent can then be recycled to the reaction mixture while the methanol or ethanol solution is stored for subsequent disposal or recovery.

The combination of techniques described above permits the preparation of higher esters of carboxylic acids by transesterification as "bottoms" products on an industrial scale. In addition to significantly high product yields, it is now possible to obtain the ester essentially free of the organotin reaction catalyst.

The following non-limiting examples set forth hereinbelow illustrate certain aspects of the present invention. They are not to be considered limiting as to the scope and nature of the present invention. In the examples which follow, all parts are parts by weight, and the term "molar ratio" refers to the molar ratio of alkali to dimethyltin dichloffde.

EXAMPLES

Multifunctional acrylates and methacrylates were prepared by the organotin catalyzed transesterification process (as described in the examples below) and were compared to samples obtained from Aldrich Chemical Company. Aldrich generally obtains the purest possible chemicals available from commercial sources for catalog sales. Lot numbers and Certificates of Analyses were obtained with each Aldrich sample. Puffties claimed by Aldrich and other manufacturers of multifunctional acrylates and methacrylates are listed in Table I. The analytical test method used by Aldrich for the analysis of each sample was reported by Aldrich as follows:

Column: 30 meter DB-1 (J&W) methyl silicone capillary

Injection Temperature: 280° C.

Column Temperature: 180° C.–280° C.

Temperature Ramp: 10° C./minute

Preprogram Hold: 0 minutes

Postprogram Hold: 10 minutes

Detector: Flame Ionization Detector

Detector Temperature: 300° C.

Solvent: Neat or chloroform

Aldrich modifies the above assay method for HDDA and TMPTMA as follows:

| Compound | Change |
| --- | --- |
| 1,6-Hexanediol Diacrylate (HDDA) | Column Temp: 130° C.–280° C. |
| Trimethylolpropane Trimethacrylate (TMPTMA) | Injection Temp: 300° C. Column Temp: 200° C.–300° C. |

Aldrich's analytical test method does not differ appreciably from the standard analytical test method used by Sartomer Chemical Company to report purity and confirm that product specifications have been met. However, the heat history of the sample during analysis by Sartomer's GC method is more severe than the heat history of the sample during analysis by Aldrich's GC method, leading to even more extensive GC column chemistry changes, which results in the absence or diminution of higher boiling "heavy" peaks that would otherwise be observed under milder GC column conditions.

The chromatogram obtained using an 11 meter RTX200 megabore gas chromatographic column with an injection port temperature of only 200° C. is substantially different than the chromatogram obtained using the GC test programs of Sartomer or Aldrich. Results obtained using the 11 meter RTX200 megabore gas chromatographic column are consistent with those obtained by more accurate, reliable and unbiased analytical techniques, such as HPLC techniques using an RI detector under isocratic conditions and the combined Size Exclusion Chromatography (SEC)—High Performance Liquid Chromatography (HPLC) technique of R. H. Hall (Radcure Europe 1985 Conference).

In Table 1 and in the examples reported below, the purities of the products made by the organotin catalyzed transesterification process are compared with other available products. The gas chromatographic conditions used to analyze all samples are as follows:

GC Apparatus: Varian 3700 or Hewlett Packard 5890

Column: 11 meter RTX200 (trifluoropropyl methyl polysiloxane) film thickness (df)—1.0 micrometer, Restek Corporation, Catalogue #15055

Injection Volume: 0.5 microliter of a 1.0% solution of sample in methylene chloride Injection Temperature: 200° C.

Detector Temperature: 300° C.

Carrier Gas: helium at 8.5 to 8.8 cc per minute

Make-up Gas: helium at 21.2 to 21.5 cc per minute $H_2$ for Detector: 27.5 to 30.0 cc per minute Air for Detector: 400 to 416 cc per minute Split Ratio: 1.0 (Vent flow=0)

Range (Oven/Column): Varian=10 (−11 power), HP=5.0

The temperature program was the same in all cases. The column temperature was held at 90° C. for 2 minutes and then raised to 270° C. at a rate of 8° C. per minute.

TABLE 1

| Example Number | Product | Source | Claimed Purity (GC %) | Purity (GC %) 11 m RTx200 |
| --- | --- | --- | --- | --- |
| 1 | TMPTA | OCT* | — | 99 |
|  |  | Aldrich | 88 | 79 |
|  |  | UCB** | no claim | 78 |
|  |  | Sartomer | 91 | 77 |
| 2 | TPGDA | OCT | — | 99 |
|  |  | Aldrich | 91 | 87 |
|  |  | UCB | no claim | 87 |
| 3 | T4EGDA | OCT | — | 99 |
|  |  | Aldrich | 88 | 86 |
| 4 | HDDA | OCT | — | 99 |
|  |  | Aldrich | 91 | 91 |
|  |  | UCB | no claim | 90 |
| 5 | 1,3-BGDA | OCT | — | 99 |
|  |  | SP2*** | no claim | 82 |
| 6 | PEA | OCT | — | 99 |
|  |  | Aldrich | 86 | 87 |
| 7 | TMPTMA | OCT | — | 99 |
|  |  | Aldrich | 90 | 88 |
| 8 | PEG200DMA | OCT | — | 99 |
|  |  | SP2 | no claim | 87 |
| 9 | T4EGDMA | OCT | — | 99 |
|  |  | Aldrich | 94 | 90 |
| 10 | 1,3-BGDMA | OCT | — | 99 |
|  |  | Aldrich | 90 | 90 |

*OCT = organotin catalyzed transesterification process
**UCB = UCB Radcure Incorporated.
***$SP^2$ = Scientific Polymer Products, Inc.

Example 1

Preparation of trimethylolpropane triacrylate (TMPTA)

A flask was charged with a mixture of 268.4 parts of trimethylolpropane, 901.1 parts ethyl acrylate, 100.8 parts of heptane, polymerization inhibitors, 19.8 parts of a 50% solution of dimethyltin dichloride in methanol and 8 parts of a 25% solution of sodium methoxide in methanol.

The mixture was heated to reflux, using a rectifying column topped by a varying reflux head to remove the ethanol in the form of its azeotrope with heptane. The reaction was considered to be complete when the ratio of triester to diester, as determined by GC, was greater than 100:1. The product was washed with aqueous sodium hydroxide solution to remove the catalyst and the polymerization inhibitors. The excess ethyl acrylate and heptane were removed by distillation.

The final product had a purity of 99% (as analyzed using the 11 meter RTX200 column) and a Brookfield (LV series) viscosity of 45 cps (25° C., #1 Spindle, 60 rpm) with a 97% yield. By comparison, commercially available samples of TMPTA (Aldrich, UCB and Sartomer) had purities ranging from 77% to 79% (as analyzed using the 11 meter RTX200 column) and a Brookfield (LV series) viscosity of 110 (25° C., #1 Spindle, 30 rpm).

Example 2

Preparation of tripropylene glycol diacrylate (TPGDA)

A flask was charged with a mixture of 153.8 parts of tripropylene glycol, 240.3 parts of ethyl acrylate, 33.4 parts of heptane, polymerization inhibitors, 10.5 parts of a 50% solution of dimethyltin dichloride in methanol and 3.8 parts of a 25% solution of sodium methoxide in methanol.

The mixture was heated to reflux, using a rectifying column topped by a varying reflux head to remove the ethanol in the form of its azeotrope with heptane. The reaction was considered to be complete when the ratio of diester to monoester, as determined by GC, was greater than 100:1. The product was washed with aqueous sodium hydroxide solution to remove the catalyst and the polymerization inhibitors. The excess ethyl acrylate and heptane were removed by distillation.

The final product had a purity of 99% (as analyzed using the 11 meter RT×200 column) and an APHA (ASTM D-1209) color of 30 with a 92% yield. By comparison, commercially available samples of TPGDA (Aldrich and UCB) had a purity of of 87% (as analyzed using the 11 meter RT×200 column) and an APHA color of 70.

Example 3

Preparation of tetraethylene glycol diacrylate (T4EGDA)

A flask was charged with a mixture of 184.2 parts of tetraethylene glycol, 344.4 parts of methyl acrylate, polymerization inhibitors, 5.1 parts of a 50% solution of dimethyltin dichloride in methanol and 2 parts of a 25% solution of sodium methoxide in methanol.

The mixture was heated to reflux, using a rectifying column topped by a varying reflux head to remove the methanol in the form of its azeotrope with methyl acrylate. The reaction was considered to be complete when the ratio of diester to monoester, as determined by GC, was greater than 100:1. The product was washed with aqueous sodium hydroxide solution to remove the catalyst and the polymerization inhibitors. The excess methyl acrylate was removed by distillation.

The final product had a purity of 99% (as analyzed using the 11 meter RT×200 column) and an APHA color of 50 with an 89% yield. By comparison, a commercially available sample of T4EGDA (Aldrich) had a purity of 86% (as analyzed using the 11 meter RT×200 column) and an APHA color of 100.

Example 4

Preparation of 1,6-hexanediol diacrylate (HDDA)

A flask was charged with a mixture of 1182 parts of 1,6-hexanediol, 2152 parts of methyl acrylate, polymerization inhibitors, 250 parts of heptane, 20 parts of a 50% solution of dimethyltin dichloride in methanol and 10 parts of a 25% solution of sodium methoxide in methanol.

The mixture was heated to reflux, using a rectifying column topped by a varying reflux head to remove the methanol in the form of its azeotrope with heptane. The reaction was considered to be complete when the ratio of diester to monoester, as determined by GC, was greater than 100:1. The product was washed with aqueous sodium hydroxide solution to remove the catalyst and the polymerization inhibitors. The excess methyl acrylate and heptane solvent were removed by distillation.

The final product had a purity of 99% (as analyzed using the 11 meter RT×200 column) and an APHA color of 10 with a 96% yield. By comparison, commercially available samples of HDDA (Aldrich and UCB) had purities ranging from 90 to 91% (as analyzed using the 11 meter RT×200 column) and an APHA color of 20.

Example 5

Preparation of 1,3-butylene glycol diacrylate (1,3-BGDA)

A flask was charged with a mixture of 90.1 parts of 1,3-butylene glycol, 258.3 parts of methyl acrylate, 44 parts of cyclohexane, polymerization inhibitors, 4.0 parts of a 50% solution of dimethyltin dichloride in methanol and 2.1 parts of a 25% solution of sodium methoxide in methanol.

The mixture was heated to reflux, using a rectifying column topped by a varying reflux head to remove the methanol in the form of its azeotrope with cyclohexane. The reaction was considered to be complete when the ratio of diester to monoester, as determined by GC, was greater than 100:1. The product was washed with aqueous sodium hydroxide solution to remove the catalyst and the polymerization inhibitors. The excess methyl acrylate and cyclohexane solvent were removed by distillation.

The final product had a purity of 99% (as analyzed using the 11 meter RT×200 column) and an APHA color of 20 with a 93% yield. By comparison, a commercially available sample of 1,3 BGDA (Scientific Polymer Products) had a purity of 82% (as analyzed using the 11 meter RT×200 column) and an APHA color of 250 to 300.

Example 6

Preparation of 2-phenoxyethyl acrylate (PEA)

A flask was charged with a mixture of 1182 parts of 2-phenoxyethanol, 2152 parts of methyl acrylate, polymerization inhibitors, 250 parts of heptane, 20 parts of a 50% solution of dimethyltin dichloride in methanol and 10 parts of a 25% solution of sodium methoxide in methanol.

The mixture was heated to reflux, using a rectifying column topped by a varying reflux head to remove the methanol in the form of its azeotrope with heptane. The reaction was considered to be complete when the ratio of ester to alcohol, as determined by GC, was greater than 100:1. The product was washed with aqueous sodium hydroxide solution to remove the catalyst and the polymerization inhibitors The excess methyl acrylate and heptane solvent were removed by distillation.

The final product had a purity of 99% (as analyzed using the 11 meter RT×200 column) and an APHA color of 5 with a 96% yield. By comparison, a commercially available sample of PEA (Aldrich) had a purity of 87% (as analyzed using the 11 meter RT×200 column) and an APHA color of 15.

Example 7

Preparation of trimethylolpropane trimethacrylate (TMPTMA)

A flask was charged with a mixture of 268.2 parts of trimethylolpropane, 801 parts methyl methacrylate, 123.5 parts of heptane, polymerization inhibitors, 24 parts of a 50% solution of dimethyltin dichloride in methanol and 12.8 parts of a 25% solution of sodium methoxide in methanol.

The mixture was heated to reflux, using a rectifying column topped by a varying reflux head to remove the methanol in the form of its azeotrope with heptane. The reaction was considered to be complete when the ratio of triester to diester, as determined by GC, was greater than 100:1. The product was washed with aqueous sodium hydroxide solution to remove the catalyst and the polymerization inhibitors. The excess methyl methacrylate and heptane solvent were removed by distillation.

The final product had a purity of 99% (as analyzed using the 11 meter RT×200 column) and an APHA color of 5 with a 99% yield. By comparison, a commercially available sample of TMPTMA (Aldrich) had a purity of 88% (as analyzed using the 11 meter RT×200 column) and an APHA color of 100 to 150.

Example 8

Preparation of polyethylene glycol dimethacrylate (PEG200DMA)

A flask was charged with a mixture of 408 parts of polyethylene glycol (having an average molecular weight of 200 Daltons and consisting predominantly of diethylene glycol (EG2), triethylene glycol (EG3), tetraethylene glycol (EG4), pentaethylene glycol (EG5), hexaethylene glycol (EG6) and heptaethylene glycol (EG7)), 670 parts of methyl methacrylate, 83 parts of cyclohexane, polymerization inhibitors, 13.3 parts of a 50% solution of dimethyltin dichloride in methanol and 5.3 parts of a 25% solution of sodium methoxide in methanol.

The mixture was heated to reflux, using a rectifying column topped by a varying reflux head to remove the methanol in the form of its azeotrope with cyclohexane. The reaction was considered to be complete when the ratio of diester to monoester, as determined by GC, was greater than 74:1 for EG2, 62:1 for EG3 and 47:1 for EG4. The product was washed with aqueous sodium hydroxide solution to remove the catalyst and the polymerization inhibitors. The excess methyl methacrylate and cyclohexane solvent were removed by distillation.

The final product (the dimethacrylates of EG2, EG3, EG4, EG5, EG6 and EG7) had a purity of 99% (as analyzed using the 11 meter RT×200 column) and an APHA color of 20 with a 93% yield. By comparison, a commercially available sample of PEG200DMA (Scientific Polymer Products) had a purity of 87% (as analyzed using the 11 meter RT×200 column) and an APHA color of 35.

Example 9

Preparation of tetraethylene glycol dimethacrylate (T4EGDMA)

A flask was charged with a mixture of 184.2 parts of tetraethylene glycol, 300 parts of methyl methacrylate, 42 parts of cyclohexane, polymerization inhibitors, 5.1 parts of a 50% solution of dimethyltin dichloride in methanol and 2 parts of a 25% solution of sodium methoxide in methanol.

The mixture was heated to reflux, using a rectifying column topped by a varying reflux head to remove the methanol in the form of its azeotrope with cyclohexane. The reaction was considered to be complete when the ratio of diester to monoester, as determined by GC, was greater than 100:1. The product was washed with aqueous sodium hydroxide solution to remove the catalyst and the polymerization inhibitors. The excess methyl methacrylate and cyclohexane solvent were removed by distillation.

The final product had a purity of 99% (as analyzed using the 11 meter RT×200 column) and an APHA color of 25 with a 91% yield. By comparison, a commercially available sample of T4EGDMA (Aldrich) had a purity of 90% (as analyzed using the 11 meter RT×200 column) and an APHA color of 50.

Example 10

Preparation of 1,3-butylene glycol dimethacrylate (1,3-BGDMA)

A flask was charged with a mixture of 90.1 parts of 1,3-butylene glycol, 300 parts of methylmethacrylate, 52 parts of cyclohexane, polymerization inhibitors, 4 parts of a 50% solution of dimethyltin dichloride in methanol and 2.1 parts of a 25% solution of sodium methoxide in methanol.

The mixture was heated to reflux, using a rectifying column topped by a varying reflux head to remove the methanol in the form of its azeotrope with cyclohexane. The reaction was considered to be complete when the ratio of diester to monoester, as determined by GC, was greater than 100:1. The product was washed with aqueous sodium hydroxide solution to remove the catalyst and the polymerization inhibitors. The excess methyl methacrylate and cyclohexane were removed by distillation.

The final product had a purity of 99% (as analyzed using the 11 meter RT×200 column) and an APHA color of 20 with a 91.4% yield. By comparison, a commercially available sample of 1,3-BGDMA (Aldrich) had a purity of 90% (as analyzed using the 11 meter RT×200 column) and an APHA color of 80.

Many other analytical techniques corroborate the enhanced purity of the TMPTA produced using the organotin catalyzed transesterification process compared to the TMPTA produced by Aldrich, UCB Radcure and Sartomer. When these same samples of TMPTA are analyzed by Fourier Transform Infrared Spectroscopy (FTIR), the most significant differences occur in the —OH (alcohol) transmission spectrum at 3540 wave number ($cm^{-1}$). The —OH (alcohol) content of the TMPTA produced by the organotin catalyzed transesterification process is virtually absent in contrast to the substantial —OH (alcohol) content of the TMPTA produced by Aldrich, Sartomer and UCB. The absence of —OH (alcohol) content of the TMPTA produced by the organotin catalyzed transesterification process indicates that the degree of conversion of alcohol to ester and the final product purity of TMPTA is much higher when producing TMPTA by the organotin catalyzed transesterification process than by the esterification processes of Aldrich, Sartomer and UCB (or their suppliers).

The analysis of TMPTA samples by an acetonitrile/water gradient elution High Performance Liquid Chromatography (HPLC) technique which uses a Photo Diode Array (PDA) detector enables one to identify the optimum wavelength of ultraviolet (UV) light for detection of all the components in the TMPTA samples. Although the presence of substantial quantities of heavy boiling components in the Aldrich, UCB and Sartomer TMPTA samples can be verified qualitatively, the exact purity of the these components cannot be precisely quantified by an HPLC gradient elution technique using a UV detector because the determination of response factors for all components of the TMPTA samples is not possible. The determination of response factors for all components of the TMPTA samples is not possible due to the unavailability, either commercially or by laboratory synthesis methods, of standard samples of known purity for all components of the TMPTA samples.

However, analysis of TMPTA samples from Aldrich, UCB Radcure and Sartomer by HPLC gradient elution using a UV detector are readily distinguished from similarly analyzed samples of TMPTA made by the organotin catalyzed transesterification process by the absence of late eluting components in the TMPTA samples made by the organotin catalyzed transesterification process. Significantly, the Aldrich, UCB and Sartomer TMPTA samples have substantial amounts of high boiling, late eluting impurities which comprise approximately 25% of the integrated area of their chromatograms.

It is of great significance that the analysis of TMPTA samples from Aldrich, UCB Radcure and Sartomer by HPLC under isocratic conditions with a mobile phase consisting of 70% acetonitrile and 30% water and using a UV detector in series with a refractive index (RI) detector provides reliable, unbiased quantitative results. This analytical technique also readily distinguishes samples of TMPTA made by the organotin catalyzed transesterification process from the TMPTA samples from Aldrich, UCB Radcure and Sartomer. The HPLC isocratic conditions are as follows:

HPLC Apparatus: Hewlett-Packard HP 1050 Pump with an HP 1050 UV detector in series with an HP 1047A Refractive Index (RI) detector Mobile Phase: 70% Acetonitrile, 30% Water Sample Dilution: 0.1 grams sample per 40 ml mobile phase Injection Volume: 20 microliters Flow Rate: 1.0 ml per minute Column Temp: 40° C.

RI Detector Temp: 40° C.

UV Detector: Wavelength=215 nm

RI Detector: Total signal to integrator

In the HPLC chromatograms, the integrated area percentages for the chromatogram peaks of the early eluting components, TMPTA and the late eluting components for each of the samples are as follows:

|  | Detector | Early Eluting Peaks (Area %) | TMPTA (Area %) | Late Eluting Peaks (Area %) |
|---|---|---|---|---|
| OCT* | RI | 4 | 96 | 0 |
| UCB | RI | 5 | 69 | 25 |
| Sartomer | RI | 3 | 72 | 26 |
| Aldrich | RI | 7 | 70 | 23 |
| OCT* | UV | 3 | 97 | 1 |
| UCB | UV | 2 | 75 | 23 |
| Sartomer | UV | 4 | 71 | 23 |
| Aldrich | UV | 8 | 77 | 15 |

*OCT — organotin catalyzed transesterification

A UV detector alone provides semiquantitative purity results with an inherent bias to overestimate the purity of TMPTA because of the differential response to excitation by UV light of the higher boiling Michael adduct components and lighter boiling components viz a viz TMPTA. This diffential excitation response is minimized by using the optimal UV wavelength (average of 215 nm for the analyzed TMPTA samples) as determined by the HPLC technique using a PDA detector described above.

However, an RI detector is a mass sensitive detector which responds only to differences in concentration when the mobile phase solvent is of constant composition. In other words, the results of HPLC techniques with an RI detector under isocratic conditions can be interpreted as giving unbiased purity results. Using an HPLC technique eliminates the high column temperatures required by GC techniques which result in unpredictable GC column chemistry changes that consistently bias GC results in the direction of giving higher TMPTA purity levels than are actually present in the sample being analyzed.

The 11 meter RTX200 trifluoropropylmethyl polysiloxane column GC technique described above minimizes this bias and substantially reduces this bias as compared to the methyl silicone column GC techniques of Sartomer and Aldrich. When the chromatograms of Aldrich, UCB and Sartomer TMPTA samples analyzed using the 11 meter RTX200 column GC technique are compared to the chromatograms of TMPTA samples made by the organotin catalyzed transesterification process and analyzed using the same 11 meter RTX200 trifluoropropylmethyl polysiloxane colunto GC technique, the results are similar to those obtained using the above described HPLC gradient elution techniques with a UV detector and HPLC techniques with a UV and RI detector in series under isocratic conditions. The common thread of the analyses using the 11 meter RTX200 column GC technique and all the HPLC analytical techniques is that higher boiling "heavies" are virtually absent in the TMPTA made by the organotin catalyzed transesterificaton process, but are present as impurities at levels of approximately 20 to 25% in the samples of Aldrich, UCB and Sartomer TMPTA.

Equivalently corroborative results are expected for the other monomers of the present invention.

As will now be readily appreciated, the present invention provides esters of carboxylic acids via transesterification, that ordinarily could not be obtained by direct esterification. The present invention also provides 1,2- and 1,3-polyol esters that, until now, could not even be; made by transesterification. Preferred embodiments of the present invention provide a simplified method for removing organotin catalyst from the carboxylic acid ester reaction product, which at the same time removes excess polymerization inhibitors. The present invention, therefore, satisties a long-felt and heretofore unmet need for organotin catalyst-free transesterification reaction products, in general, and for 1,2- and 1,3-polyol ester reaction products in particular.

The foregoing description of the preferred embodiment should be taken as illustrating, rather than as limiting, the present invention as defined by the claims. Numerous variations and combinations of the features described above can be utilized without departing from the present invention.

What is claimed is:

1. An ester of an acrylic or methacrylic acid with an alcohol or polyol, which ester is selected from the group consisting of trimethylolpropane triacrylate, tripropylene glycol diacrylate, tetraethylene glycol diacrylate, 1,6-hexanediol diacrylate, 1,3-butylene glycol diacrylate, 2-phenoxyethyl acrylate, trimethylolpropane trimethacrylate, polyethylene glycol dimethacrylate, tetraethylene glycol dimethacrylate and 1,3-butylene glycol dimethacrylate, wherein said ester has a level of purity greater than about 95% as measured by gas chromatography using an 11 meter RTX200 trifluoropropyl methyl polysiloxane column, a flame ionization detector, an injection temperature of 200° C., an initial column temperature of 90° C. for two minutes, followed by heating to 270° C. at a rate of 8° C. per minute and a detector temperature of 300° C.

2. The ester of claim 1, having a level of purity between about 97% and about 99%.

3. The ester of claim 1, substantially free of organotin reaction catalysts and polymerization inhibitors.

4. The ester of claim 3, having an organotin level less than about 100 ppm.

5. The ester of claim 4, wherein said organotin level is less than about 10 ppm.

6. The ester of claim 1, consisting of trimethylolpropane triacrylate.

7. The ester of claim 1, consisting of tripropylene glycol diacrylate.

8. The ester of claim 1, consisting of tetraethylene glycol diacrylate.

9. The ester of claim 1, consisting of 1,6-hexanediol diacrylate.

10. The ester of claim 1, consisting of 1,3-butylene glycol diacrylate.

11. The ester of claim 1, consisting of 2-phenoxyethyl acrylate.

12. The ester of claim 1, consisting of trimethylolpropane trimethacrylate.

13. The ester of claim 1, consisting of polyethylene glycol dimethacrylate.

14. The ester of claim 1, consisting of tetraethylene glycol dimethacrylate.

15. The ester of claim 1, consisting of 1,3-butylene glycol dimethacrylate.

16. Trimethylolpropane triacrylate having a level of purity greater than about 92% as measured by gas chromatography using an 11 meter RTX200 trifluoropropylmethyl polysiloxane column, a flame ionization detector, an injection temperature of 200° C., an initial column temperature of 90° C. for two minutes, followed by heating to 270° C. at a rate of 8° C. per minute and a detector temperature of 300° C.

* * * * *

UNITED STATES PATENT AND TRADEMARK OFFICE
CERTIFICATE OF CORRECTION

PATENT NO. : 5,554,785
DATED : September 10, 1996
INVENTOR(S) : Trapasso et al.

It is certified that error appears in the above-identified patent and that said Letters Patent is hereby corrected as shown below:

On the title page, under "Related U.S. Application Data" "[63]", "Sep. 19, 1993" should read —Sep. 3, 1993—.

Column 3, line 34, "purifies" should read --purities--.

Column 10, line 67, "tings" should read --rings--.

Column 12, line 49, "dichloffde" should read --dichloride--.

Column 12, line 60, "Puffties" should read --Purities--.

Column 19, line 52, "colunto" should read --column--.

Column 20, line 2, "be; made" should read --be made--.

Column 20, line 7, "satisties" should read --satisfies--.

Signed and Sealed this

Twenty-fourth Day of December, 1996

Attest:

BRUCE LEHMAN

Attesting Officer    Commissioner of Patents and Trademarks